(12) United States Patent
Beato et al.

(10) Patent No.: US 10,737,251 B2
(45) Date of Patent: Aug. 11, 2020

(54) CATALYST COMPRISING SMALL 10-RING ZEOLITE CRYSTALLITES AND A METHOD FOR PRODUCING HYDROCARBONS BY REACTION OF OXYGENATES OVER SAID CATALYST

(71) Applicant: HALDOR TOPSØE A/S, Kgs. Lyngby (DK)

(72) Inventors: Pablo Beato, København (DK); Stian Svelle, Oslo (NO); Daniel Rojo Gama, Palencia (ES); Andrea Molino, Montaldo Roero (IT); Katarzyna Anna Lukaszuk, Oslo (NO); Wegard Skistad, Åmot (NO)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/323,981

(22) PCT Filed: Sep. 28, 2017

(86) PCT No.: PCT/EP2017/074662
§ 371 (c)(1),
(2) Date: Feb. 7, 2019

(87) PCT Pub. No.: WO2018/060349
PCT Pub. Date: Apr. 5, 2018

(65) Prior Publication Data
US 2019/0176136 A1 Jun. 13, 2019

(30) Foreign Application Priority Data
Sep. 30, 2016 (DK) .................. 2016 00578

(51) Int. Cl.
| | | |
|---|---|---|
| *B01J 29/06* | (2006.01) |
| *B01J 29/70* | (2006.01) |
| *B01J 35/02* | (2006.01) |
| *C01B 39/48* | (2006.01) |
| *C07C 1/20* | (2006.01) |
| *C10G 11/00* | (2006.01) |
| *C10G 3/00* | (2006.01) |
| *B01J 37/03* | (2006.01) |
| *B01J 37/10* | (2006.01) |
| *C07C 1/24* | (2006.01) |
| *B01J 35/00* | (2006.01) |
| *C07C 11/02* | (2006.01) |

(52) U.S. Cl.
CPC ....... *B01J 29/7046* (2013.01); *B01J 29/7042* (2013.01); *B01J 35/023* (2013.01); *B01J 37/031* (2013.01); *B01J 37/10* (2013.01); *C01B 39/48* (2013.01); *C07C 1/20* (2013.01); *C07C 1/24* (2013.01); *C10G 3/49* (2013.01); *C10G 11/00* (2013.01); *B01J 35/002* (2013.01); *C01P 2002/72* (2013.01); *C07C 11/02* (2013.01); *C07C 2529/70* (2013.01); *C10G 2300/1011* (2013.01); *C10G 2300/1022* (2013.01); *C10G 2400/02* (2013.01); *C10G 2400/20* (2013.01); *C10G 2400/22* (2013.01)

(58) Field of Classification Search
CPC .. B01J 29/7042; B01J 29/7046; B01J 35/023; B01J 35/002; B01J 37/031; B01J 37/10; C10G 3/49; C10G 11/00; C10G 11/02; C10G 2400/22; C10G 2400/02; C07C 1/20; C07C 1/24; C07C 2529/70; C01P 2002/72; C01B 39/48
USPC ..... 502/60, 77; 423/704, 705, 706; 585/638, 585/639, 640
See application file for complete search history.

(56) References Cited

U.S. PATENT DOCUMENTS

| | | | |
|---|---|---|---|
| 4,490,342 A | 12/1984 | Valyocsik | |
| 4,870,038 A | 9/1989 | Page et al. | |
| 4,929,790 A | 5/1990 | Kaeding et al. | |
| 5,063,038 A | 11/1991 | Kirker et al. | |
| 5,157,194 A | 10/1992 | Rahmim et al. | |
| 5,332,566 A | 7/1994 | Moini | |
| 6,692,723 B2 | 2/2004 | Rouleau et al. | |
| 7,119,245 B1 * | 10/2006 | Thoma ............... | B01D 67/0051 585/820 |
| 2002/0192156 A1 | 12/2002 | Rouleau et al. | |
| 2006/0011514 A1 * | 1/2006 | van den Berge ........ | B01J 29/80 208/120.01 |
| 2008/0159953 A1 | 7/2008 | Miller | |
| 2015/0190792 A1 * | 7/2015 | Muraza ................ | B01J 29/7046 423/705 |

(Continued)

FOREIGN PATENT DOCUMENTS

| | | |
|---|---|---|
| CN | 1766053 A | 5/2006 |
| WO | 2017105617 A1 | 6/2017 |

OTHER PUBLICATIONS

Chen, Lei, et al., "Hydrothermal synthesis of nanosized ZSM-22 and their use in the catalytic conversion of methanol", Chinese Journal of Catalysis/Dalian Institute of Chemical Physics, Aug. 5, 2015, pp. 1381-1388, vol. 37, No. 8.

(Continued)

*Primary Examiner* — Elizabeth D Wood

(74) *Attorney, Agent, or Firm* — Buchanan Ingersoll & Rooney P.C.

(57) ABSTRACT

A catalyst material comprising 10-ring zeolite crystallites with one-dimensional non-intersecting channels wherein, the crystallites have an average length of less than 150 nm. The catalysts are useful in a method for producing hydrocarbons by reaction of oxygenates over said catalysts.

21 Claims, 3 Drawing Sheets

(56) References Cited

U.S. PATENT DOCUMENTS

Figure 1:
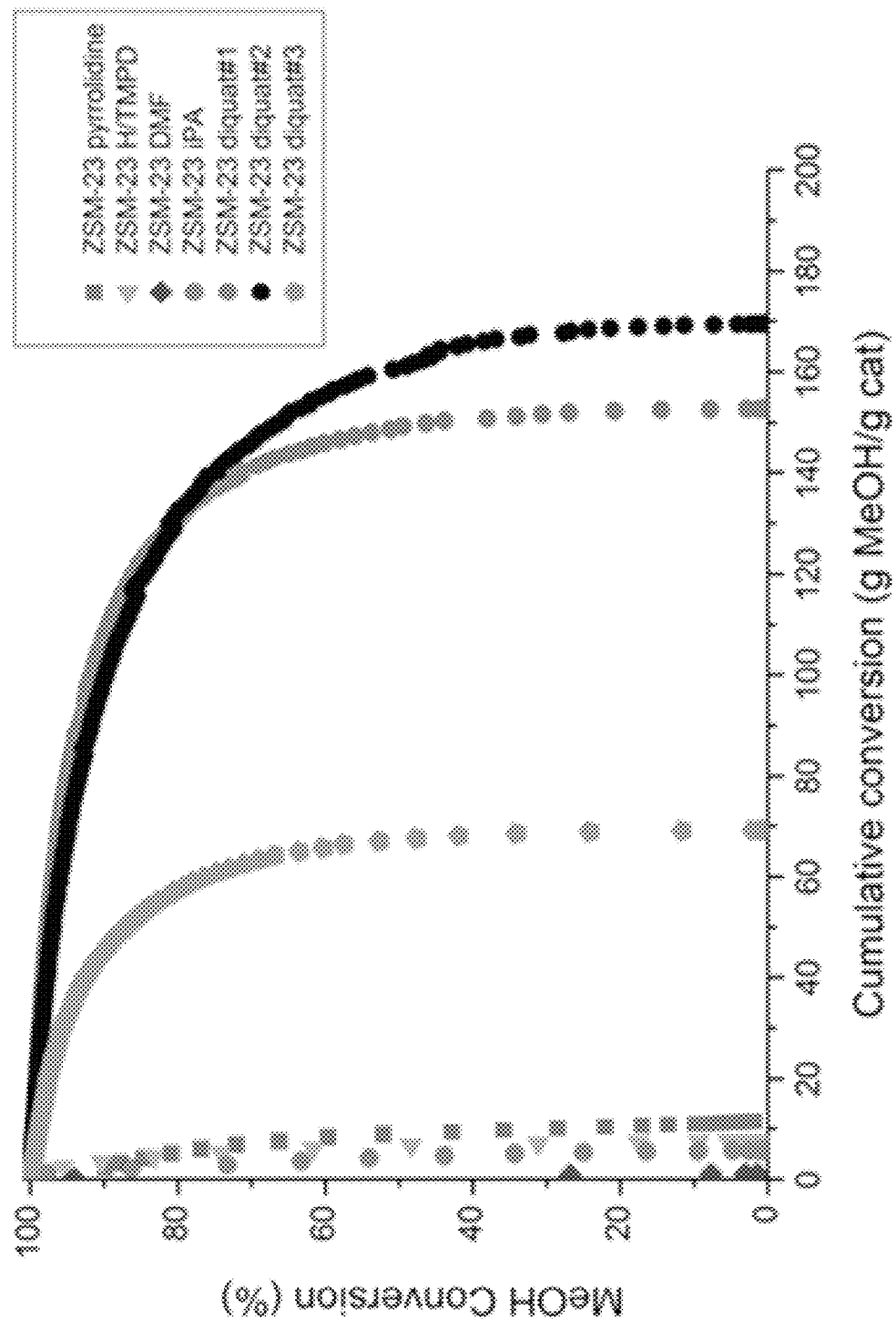

2015/0360964 A1* 12/2015 Rimer .................. C01B 39/54
423/700

OTHER PUBLICATIONS

Jamil, Anas K., et al., "Selective Production of Propylene from Methanol Conversion over Nanosized ZSM-22 Zeolites", Industrial & Engineering Chemistry Research, Dec. 5, 2014, pp. 19498-19505, vol. 52, No. 50.

Molino, A., et al., "Conversion of methanol to hydrocarbons over zeolite ZSM-23 (MTT): exceptional effects of particle size on catalyst lifetime", Chemical Communications, May 17, 2017, pp. 6816-6819, vol. 53, No. 51.

Wang, Jinbang, et al., "An approach to prepare nanosized HZSM-22 with enhanced lifetime in the methanol hydrocarbon (MTH) reaction", RSC Advances, Oct. 15, 2015, pp. 88928-88935, vol. 5, No. 108.

International Search Report (PCT/ISA/210) dated Mar. 21, 2018, by the European Patent Office as the International Searching Authority for International Application No. PCT/EP2017/074662.

Written Opinion (PCT/ISA/237) dated Mar. 21, 2018, by the European Patent Office as the International Searching Authority for International Application No. PCT/EP2017/074662.

Danish Search Report for corresponding Danish Application No. PA 2016 00578 dated May 30, 2017.

Teketel, Shewangizaw, et al., "Shape Selectivity in the Conversion of Methanol to Hydrocarbons: The Catalytic Performance of One-Dimensional 10-Ring Zeolites: ZSM-22, ZSM-23, ZSM-48, and EU-1", ACS Catalysis, Nov. 14, 2011, pp. 26-37, vol. 2, No. 1.

* cited by examiner

CATALYST COMPRISING SMALL 10-RING ZEOLITE CRYSTALLITES AND A METHOD FOR PRODUCING HYDROCARBONS BY REACTION OF OXYGENATES OVER SAID CATALYST

The Methanol to Hydrocarbon (MTH) reaction is an important process in a chain of processes to convert carbon rich feedstocks such as coal, natural gas, or biomass into hydrocarbon species such as light alkenes or gasoline fuel over porous acidic zeolite and zeotype catalysts. Over the last 40 years significant research has been invested in order to achieve new zeolites with specialised selectivity and a lifetime of industrial interest.

The present invention relates to the use of a nanosized zeolite catalysts, specifically of MTT topology, in the conversion of oxygenates, specifically methanol or dimethylether, and lower olefins, specifically ethylene, propylene or butylenes, to higher hydrocarbons ranging from C5 to C10, essentially free of aromatic molecules (below 5 wt %).

Of particular interest are medium pore zeolites (pore circumference defined by 10 oxygens), such as the commercially employed ZSM-5 catalyst (10-ring intersecting channels that form a three dimensional porous network). This catalyst is used in the Mobil Methanol to Gasoline (MTG) and Topsøe Improved Gasoline Synthesis TIGAS processes and shows a high selectivity towards an aromatics rich gasoline range C5-C6+ product.

Because the MTH reaction occurs within pores of molecular dimensions, the product selectivity is highly sensitive to the size and arrangement of the channel system; this is known as product shape selectivity.

Recently, it has been demonstrated that some 10-ring zeolites with non-intersecting, one dimensional channels, such as TON (ZSM-22) and MTT (ZSM-23) also show a high selectivity towards C5-C6+, but with a very low amount of aromatics. In the absence of channel intersections, aromatics formation and especially reactivity is limited, but rapid deactivation caused by pore blocking is an issue because of the one-dimensional pore system. The cycle life-time of such one dimensional zeolites has therefore never reached more than 1-10 hours.

In a first aspect of the present invention is provided a catalyst material which provides a significantly prolonged lifetime of the resulting catalyst.

The applicant has shown that the crystallite length has a direct correlation to the life time of the catalyst material in relation to e.g. methanol conversion to hydrocarbons. Experiments have shown that for crystallites of 150 nm and shorter there is a pronounced effect of the life time.

Especially if the crystallites have an average length less than 110 nm, such as 10-100 nm the catalyst material has a significantly improved life time compared to similar type materials with longer crystallite length.

In several embodiments the Si/Al ratio of 15-200, such as 20-120, preferably 20-70 whereby is achieved generally lower hydride transfer reactions and as a consequence lower aromatic production and longer life-time. Too low values however may result in reduced activity due to lack of acidic sites.

Preferably the Length/Width ratio is <3. Spherical particles or close to spherical particles with L/W<2 with the 10-ring channels running along the long axis may be preferred.

Preferably the zeolite is ZSM-23.

The catalyst material and catalyst according to the present invention may advantageously be applied in a commercial process carried out at 1-50 bar, such as 1-20, such as 5-20 and 350-600° C., such as 400-450° C.

EXEMPLARY PREPARATION

ZSM-23 catalysts with different crystallite sizes were prepared by modifying synthetic procedures described in literature. The reported gel compositions were adjusted to obtain products with similar Si/Al ratios; in the range 20-40. Key information is presented in Table 1. The catalyst materials are labelled according to the structure directing agent (SDA) employed: ZSM-23 DMF for N,N-dimethylformamide, ZSM-23 Pyrr for Pyrrolidine, ZSM-23 iPA for isopropylamine, ZSM-23 T/HMPD for a mixture of N1,N1,N3,N3-tetramethylpropane-1,3-diamine (TMPD) and N1,N1,N3,N3,2,2-hexamethylpropane-1,3-diamine (HMPD), ZSM-23 C7 diquat as heptamethonium bromide (N,N,N,N',N',N'-hexamethylheptane-1,7-diaminium dibromide).

| Catalyst | $SiO_2$ | $Al_2O_3$ | $H_2O$ | $Na_2O$ | SDA$^a$ | Si source | Al source | SDA type | Time (h) | t ° C. |
|---|---|---|---|---|---|---|---|---|---|---|
| ZSM-23 DMF | 1 | 0.014 | 29.5 | 0.36 | 0.55 | Colloidal $SiO_2$ | $Al_2(SO_4)_3$ | DMF | 94 | 185 |
| ZSM-23 Pyrr | 1 | 0.03 | 45.5 | 0.20 | 0.45$^a$ | Fumed $SiO_2$ | $Al(NO_3)_3$ | Pyrrolidine | 66 | 180 |
| ZSM-23 iPA | 1 | 0.012 | 26.7 | 0.046 | 2 | Fumed $SiO_2$ | $NaAlO_2$ | Isopropylamine | 92 | 160 |
| ZSM-23 H/TMPD | 1 | 0.025 | 31 | 0.06 | 1 | Colloidal $SiO_2$ | $NaAlO_2$ | 30% HMPD/70% TMPD | 160 | 160 |
| ZSM-23 C7 diquat | 1 | 0.03 | 40 | 0.16 | 0.15 | Fumed $SiO_2$ | $Al(NO_3)_3$ | Heptamethoniumbromide | 335 | 160 |

In a second aspect of the present invention is provided a method for producing a catalyst material which method providing control over significant catalyst material parameters.

These and other advantages are provided by a catalyst material comprising 10-ring zeolite crystallites with one-dimensional non-intersecting channels wherein the crystallites have an average length of less than 150 nm.

As a representative example, the synthesis with C7 diquaternary templating agent heptamethoniumdibromide was carried out as follows:

In a Teflon liner 1.60 g of NaOH 50% w/w are mixed with 0.74 g of $Al(NO_3)3.18H_2O$ and 30 g of water under stirring until complete dissolution.

3.24 g of the C7 diquaternary templating agent were added to the solution under stirring 3.45 g of fumed silica (Aldrich) was added under stirring until the formation of a dense gel The remaining 10 g of water were added to the gel.

The gel mixture was then left under magnetic stirring for 3 h and then the Teflon liner was put in a stainless steel autoclave. The synthesis was performed in a tumbling oven (rotation speed 30 rpm) preheated at the temperature of 160° C. After 14 days the autoclave was quenched in cold water and the product was collected by filtration and washed several times with distilled water.

The powder was then dried overnight at 80° C. and calcined in a muffle with at ramp of 6 h from RT to 550° C. and then for 8 h while keeping the temperature constant to remove all the organic compounds trapped into the pores. The sample was then ion exchanged 3 times with a solution of 1M $NH_4NO_3$ at 80° C. for 3-5 hr. The sample in the ammonium form was then calcined again with the same condition as before.

Conversion

The conversion of methanol to hydrocarbons was performed in a continuous flow U-shaped fix-bed reactor (i.d. of 10 mm). Prior to reactions, catalysts were heated from room temperature to 550° C. under a flow of 10 mL/min of pure He. After reaching the pretreatment temperature, the flowing gas was switched to pure $O_2$ and kept for 1 hour to calcine the catalysts in-situ to remove all adsorbed species. After the pretreatment, the reactor was cooled down under a flow of pure He to the temperature applied for the reaction (400° C.).

The methanol to hydrocarbon reaction was carried out at atmospheric pressure and 400° C. 100 mg of catalyst was used (sieve fraction 250 to 420 μm). A He flow of 19.5 mL $min^{-1}$ was bubbled through a saturator filled with MeOH (BDH Laboratory, purity >99.8%) at a temperature of 20° C., giving rise to a methanol partial pressure of 130 mbar. The resulting weight hourly space velocity (WHSV) was 2 $g_{MeOH} \, g_{catalyst}^{-1} \, h^{-1}$.

The reaction products were analysed using an online Agilent 6890A gas chromatograph equipped with an SPB-5 capillary column (length 60 m, 0.530 mm i.d., stationary phase thickness of 5 μm) and a flame ionization detector (FID).

Methanol conversion, product selectivity and product yield were obtained by the integration of the areas from the GC-FID chromatogram. Both, methanol (MeOH) and dimethyl ether (DME) were considered to be reactants and the rest of compounds detected in the GC as products of reaction. Measured response factors were used for MeOH and DME, whereas the response was considered proportional to the number of carbon atoms in the molecule for the hydrocarbon products.

The catalyst performance of the 7 materials discussed here was investigated in the conversion of methanol to hydrocarbons at low feed rates. Clearly, there is a huge difference in stability and lifetime among the catalysts. This difference is quantified further by the total conversion capacities, defined as the total amount of methanol converted into hydrocarbons until complete deactivation, which are listed in Table 2.

The applicant has shown that lifetime is linked to particle dimension, and in particular the dimension in the direction of the channel system.

Thus selecting the appropriate catalyst preparation procedure according to the present invention, the lifetime of the resultant crystallites can be extended by orders of magnitude.

For the material prepared using DMF, the conversion capacity is so small that it might be more appropriate to discuss this as a stoichiometric process between methanol and acid sites. Catalysts prepared using the C7 diquaternary SDA may lead to superior catalysts. A large number of catalysts using this SDA, and the conversion capacity ranges from 60 to 180 $g_{methanol}/g_{catalyst}$.

Previous investigations of ZSM-23, and structurally related ZSM-22, report conversion capacities no higher than 16 $gg^{-1}$ at 400° C. and slightly higher at 450° C. [S. Teketel, W. Skistad, S. Benard, U. Olsbye, K. P. Lillerud, P. Beato and S. Svelle, ACS Catal., 2012, 2, 26-37][J. Wang, S. Xu, J. Li, Y. Zhi, M. Zhang, Y. He, Y. Wei, X. Guo and Z. Liu, RSC Adv., 2015, 5, 88928-88935]. Thus, compared to known methods and catalyst materials it is clear that method and catalyst materials presented here represent a significant improvement on essential parameters.

|  | BET surface area ($m^2/g$) | Si/Al from EDX | Average Crystal length from SEM (nm) | Conversion capacity ($g_{MeOH}/g_{cat}$) |
|---|---|---|---|---|
| ZSM-23 DMF | 150 | 26 | 900 | 1.1 |
| ZSM-23 Pyrrolidine | 271 | 23 | 120 | 11.6 |
| ZSM-23 iPA | 303 | 28 | 160 | 5.7 |
| ZSM-23 H/TMPD | 281 | 18 | 110 | 7.7 |
| ZSM-23 C7 Diquat#3 | 264 | 27 | 40 | 70 |

|  | BET surface area ($m^2/g$) | Si/Al from EDX | Average crystal length from SEM (nm) | Conversion capacity ($g_{MeOH}/g_{cat}$) | Ageing time | Oven |
|---|---|---|---|---|---|---|
| ZSM-23 C7 Diquat#1 | 264 | 27 | <50 nm | 153 | 24 h | Tumbling |
| ZSM-23 C7 Diquat#2 | 265 | 27 | <50 nm | 170 | 24 h | Magnetic |
| ZSM-23 C7 Diquat#3 | 265 | 27 | <50 nm | 70 | 3 h | Tumbling |

The applicant has shown that according to the present invention the life-time of a small crystal ZSM-23 (MTT topology), defined by a crystal size smaller than 100 nm can be increased by a factor of at least four compared to the currently longest reported life-times [J. Wang, S. Xu, J. Li, Y. Zhi, M. Zhang, Y. He, Y. Wei, X. Guo and Z. Liu, RSC Adv., 2015, 5, 88928-88935].

FIG. 1. shows plots of MeOH conversion over ZSM-23 catalysts at 400° C., 1 atm and WHSV of 2. From the plots it is clear that the small crystals results in significantly improved lifetimes. Also it is seen that the aging time is a relevant parameter in the production of the crystallites as the longer aging times leads to smaller crystals with longer life times.

Figure 2:
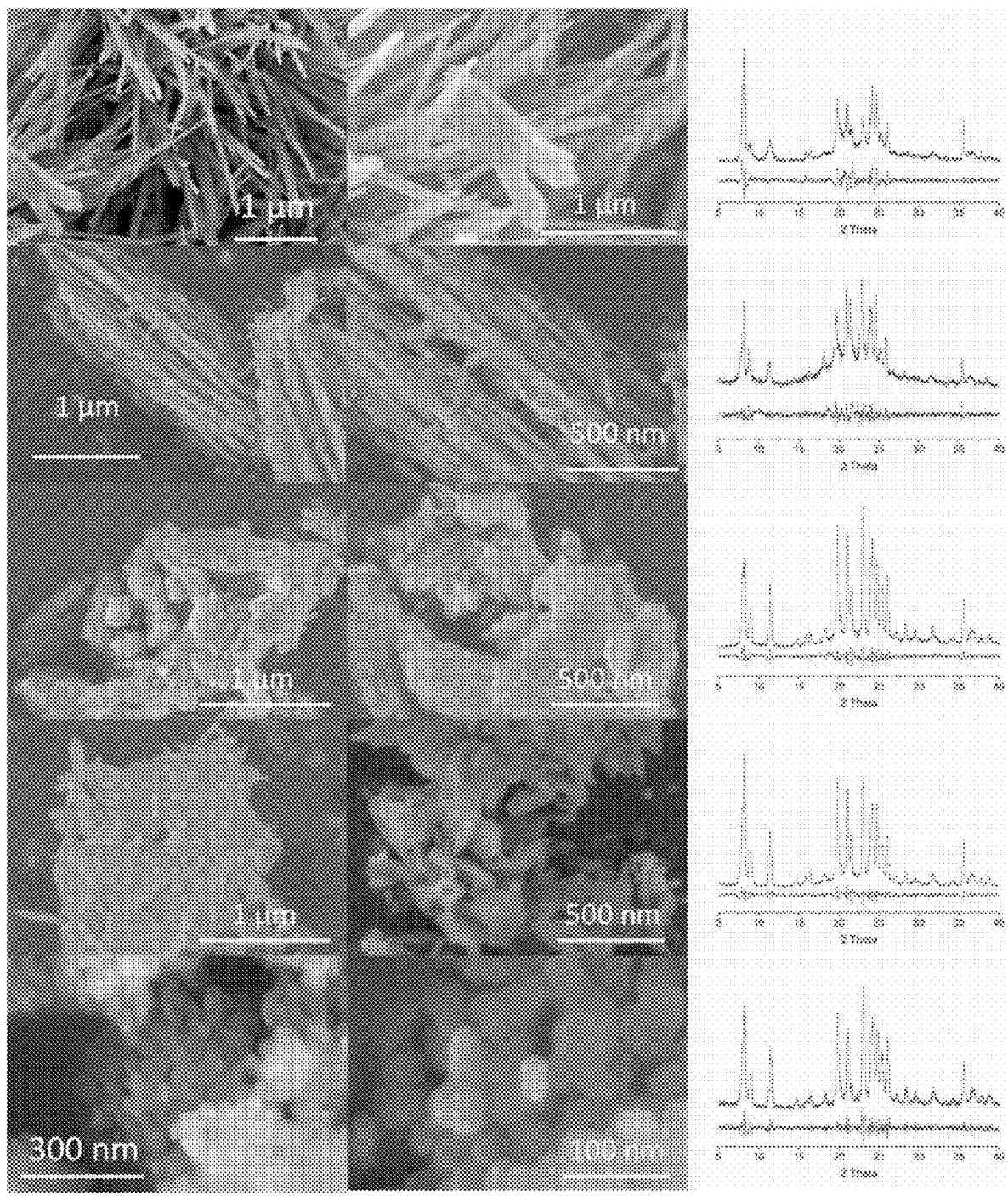

FIG. 2 Low resolution scanning electron microscopy images (left column), high resolution images (middle column) and powder X-ray diffractograms for five ZSM-23 catalysts, from top to bottom: ZSM-23 DMF, ZSM-23 pyrrolidine, ZSM-23 H/TMPD, ZSM-23 isopropylamine, ZSM-23 C7 diquat #3. The electron micrograph shows as the morphology of the crystal is spanning from micrometric sized needles (ZSM-23 DMF) to almost spherical shaped crystal with a size of tens of nanometers (ZSM-23 C7 diquat #3).

Figure 3:
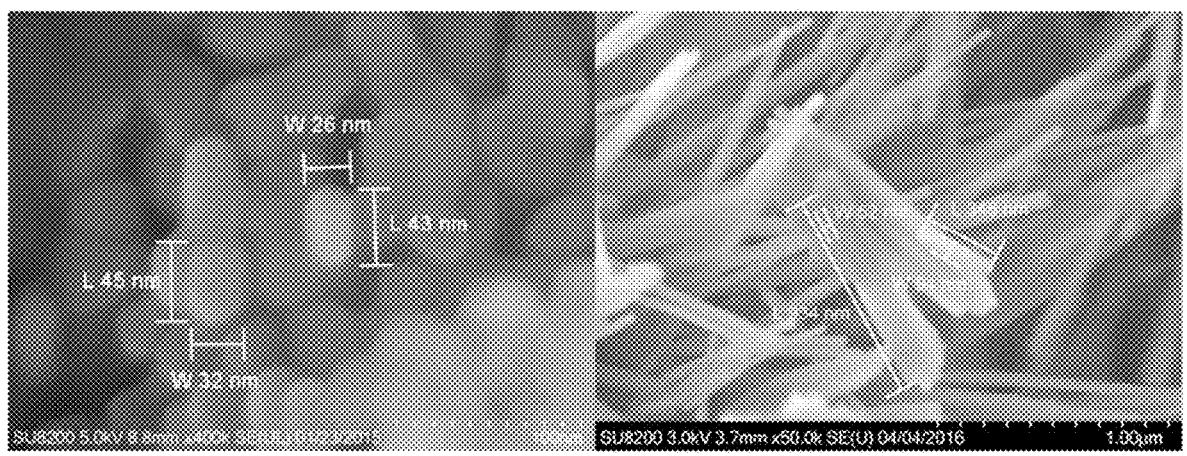

FIG. 3 SEM image of representative crystal distribution of ZSM-23 diquat #3 (left) and ZSM-23 DMF (right), with a highlight of the width (W) and length (L) of some crystals.

The invention claimed is:

1. A catalyst material comprising 10-ring zeolite crystallites with one-dimensional non-intersecting channels, wherein the crystallites have an average length of less than 50 nm, and have a Length/Width ratio of <3.

2. The catalyst material according to claim 1, having a Si/Al ratio of 15-200.

3. The catalyst material according to claim 1, wherein the Length/Width ratio is <2.

4. The catalyst material according to claim 1, wherein the zeolite is ZSM-23.

5. A catalyst comprising a catalyst material comprising 10-ring zeolite crystallites with one-dimensional non-intersecting channels, wherein the crystallites have an average length less than 50 nm, and have a Length/Width ratio of <3.

6. The catalyst according to claim 5, wherein the 10-ring zeolite crystallites have a Si/Al ratio of 15-200.

7. The catalyst according to claim 5, wherein the 10-ring zeolite crystallites have a Length/Width ratio below 2.

8. The catalyst according to claim 5, wherein the zeolite of the 10-ring zeolite crystallites is ZSM-23.

9. A catalyst material comprising 10-ring zeolite crystallites with one-dimensional non-intersecting channels, wherein the crystallites have an average length of less than 150 nm, and have a Length/Width ratio of <2.

10. A method for production of the catalyst material of claim 1, said method comprising the steps of:
obtaining a gel with a Si/Al ratio of 15-200 by
mixing a silica source and an aluminum source together with a diquaternary ammonium ion SDA in water to form a starting gel,
adjusting the pH by adding a base to the starting gel,
stir the starting gel for times from 0-40 h,
crystallization of the gel by:
heating the gel to a crystallization temperature between 150 to 180° C.,
maintain the crystallization temperature for 6 hours to 60 days,
agitate the gel during crystallization,
recover the crystalline product by filtration and washing until the pH of the filtrate is below pH 8,
dry the filtered and washed product in at least one drying step,
calcine the crystalline product,
ion exchange the calcined product at least once,
calcine the obtained NH4-form of the zeolite to obtain the H-form of the zeolite.

11. The method according to claim 10, wherein the gel is transferred to an autoclave for crystallization.

12. The method according to claim 10, wherein the filtered and washed product is dried first at room temperature and then at 100° C. for at least 12 hours.

13. The method according to claim 10, wherein the ion exchange is carried out with a 1 M solution of $NH_4NO_3$ at 60-80° C. for 3-5 h.

14. A process in which an oxygenate is converted to hydrocarbon over a catalyst according to claim 5,
wherein the hydrocarbon product comprises less than 5% aromatics,
wherein the hydrocarbon product comprises higher hydrocarbons C5 to C10,
wherein the oxygenate comprises methanol and/or DME,
wherein the process is carried out at a (WHSV) of 1-5 $g_{oxygenate} \, g_{catalyst}^{-1} \, h^{-1}$,
wherein the process is carried out at 1-50 bar,
wherein the process is carried out 350-600° C.

15. A process for producing hydrocarbons, said process comprising the step of reacting an oxygenate stream over the catalyst of claim 5, thereby producing a hydrocarbon product.

16. The process according to claim 15, wherein the hydrocarbon product comprises less than 5% aromatics.

17. The process according to claim 15, wherein the hydrocarbon product comprises higher hydrocarbons C5 to C10.

18. The process according to claim 15, wherein the oxygenate stream comprises methanol and/or DME.

19. The process according to claim 15, wherein the process is carried out at a (WHSV) of 1-5 $g_{oxygenate} \, g_{catalyst}^{-1} \, h^{-1}$.

20. The process according to claim 15, wherein the process is carried out at 1-50 bar.

21. The process according to claim 15, wherein the process is carried out 350-600° C.

* * * * *